United States Patent [19]
Rinehart et al.

[11] Patent Number: 5,908,409
[45] Date of Patent: Jun. 1, 1999

[54] TUBING PLUG

[75] Inventors: Jason D. Rinehart, Goleta; David J. Schuessler, Ventura, both of Calif.

[73] Assignee: McGhan Medical Corporation, Santa Barbara, Calif.

[21] Appl. No.: 08/921,952

[22] Filed: Aug. 26, 1997

[51] Int. Cl.$^6$ ..................................................... A61M 5/00
[52] U.S. Cl. ........................... 604/256; 604/236; 604/238; 81/426
[58] Field of Search ................................ 604/256, 236, 604/238; 81/426, 419, 15.7

[56] References Cited

U.S. PATENT DOCUMENTS

| | | | |
|---|---|---|---|
| 3,307,552 | 3/1967 | Strawn | 604/256 |
| 4,205,565 | 6/1980 | Smith | 81/15.7 |
| 4,445,896 | 5/1984 | Gianturco | 604/238 |
| 4,803,999 | 2/1989 | Liegner | 604/169 |
| 4,936,168 | 6/1990 | Willingham et al. | 81/15.7 |
| 4,982,631 | 1/1991 | Lowther | 81/426 |

*Primary Examiner*—Wynn Wood Coggins
*Assistant Examiner*—N. Kent Gring
*Attorney, Agent, or Firm*—Michael G. Petit

[57] ABSTRACT

A device for forming a leakproof closure on the terminus of a tubing having an elastic wall. The device consists of a plug insertion tool and a plug. The plug is a elongate member having a convex distal end and a proximal end. The plug insertion tool has a handle portion which is dimensioned to be grasped by a user for manipulation. The distal end of the insertion tool has a rod projecting axially therefrom which is adapted to releasably engage the proximal end of the plug. The plug is dimensioned to fit snugly within the elastically distended lumen of the tubing. In operation, the plug insertion tool is releasably attached to the proximal end of the plug by engagement means such as mating threads and the distal end of the plug inserted into the open end of the tubing and advanced by means of the insertion tool. The intralumenal portion of the plug forms a leakproof seal with the elastic wall of the tubing. The plug is inserted within the tubing and advanced until the tubing drapes over a chamfer proximal to the intralumenal portion thereof. In one sheathed embodiment the intralumenal portion of the plug includes a stepped portion which provides a detent which resists removal of the plug from the tubing. Once the plug is introduced into the tubing lumen, thereby sealing the end of the tubing, the insertion tool is detached from the proximal end of the plug thereby forming a leakproof, biocompatible and removable closure in the end of the tubing. In one embodiment, a sheath overlies the intralumenal portion of the plug. In another embodiment, the plug is of unitary construction. In yet another embodiment, the plug has the general shape of an infant pacifier.

11 Claims, 2 Drawing Sheets

TUBING PLUG

BACKGROUND OF THE INVENTION

1. Field of the Invention

This invention relates to a device for forming a closure in the end of a tubing.

2. Prior Art

There are many instances in medicine where it is desirable to implant a catheter within the body of a patient. The catheter may be used for delivering drugs into an implanted dispensing reservoir or it may be used for introducing or removing a fluid from within an inflatable article affixed in fluid communication with the open end thereof. It is of primary importance that a fluid within the tubing is not permitted to leak from the tubing even when considerable internal or external translumenal pressure is exerted on the wall of the tubing such as may occur during capsular contracture when such a tubing is surgically implanted. To prevent such undesired fluid transfer into or out of the tubing, the open end of the tubing must be sealed prior to closing the wound after implantation of the tube within the body.

Various techniques have been employed to close the open end of a tubing, such as a catheter, wherein the lumen of the tubing may need to be accessed at a later date. One such technique is the folding over or kinking of the open end of the tube and securing it in a kinked position with a non-absorbable suture. Alternatively, a clamp may be placed on the open terminus of the tubing to prevent leakage from therewithin. Upon excision, the clamp may be removed to gain access to, and establish fluid communication with, the distal end of the tubing. In many instances, the tubing is quite small; having an inner diameter of only 1–2 mm. A plug dimensioned for intraoperative insertion into the open end of such a catheter provides a challenge to even the most dexterous surgeon. A conventional plug designed to fit within the lumen of an implanted tubing would have an outer diameter of only approximately 1–2 mm, and would be difficult to grasp, hold and manipulate and easy to drop or lose in the operative field. Further, such plugs may be easily removed by internal pressure build-up within the tubing such as occurs with mammary prostheses during the well known phenomena of capsular contracture wherein the body forms a fibrous capsule around a fluid-filled inflatable member attached to the distal end of the inflation tubing. Following implantation, the capsule subsequently contracts to compress the inflatable article. For these reasons it is desirable to provide a plug for sealing the open end of a tubing which is easy to insert intraoperatively.

SUMMARY OF THE INVENTION

It is a first object of this invention to provide a plug which is readily insertable into the lumen of a tubing thereafter to form a fluid-tight closure.

It is another object of the invention to provide a device for plugging the open terminal end of a tubing, wherein following insertion, the plug is difficult to extract from the tubing without the assistance of a tool.

It is yet another object of the invention to provide a tool adapted to be attached to a plug prior to insertion and operable for inserting and removing the plug in accordance with the above objectives, and which is sufficiently large to be easily located and manipulated.

It is still another object of the invention to provide a plug which is biocompatible.

It is yet another object of the invention to provide a plug meeting the above objectives and which is self-sealing to the track of a hollow-bore needle to enable the introduction of a fluid into the tubing by injection means.

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

DESCRIPTION OF THE PREFERRED EMBODIMENTS

Figure 1:
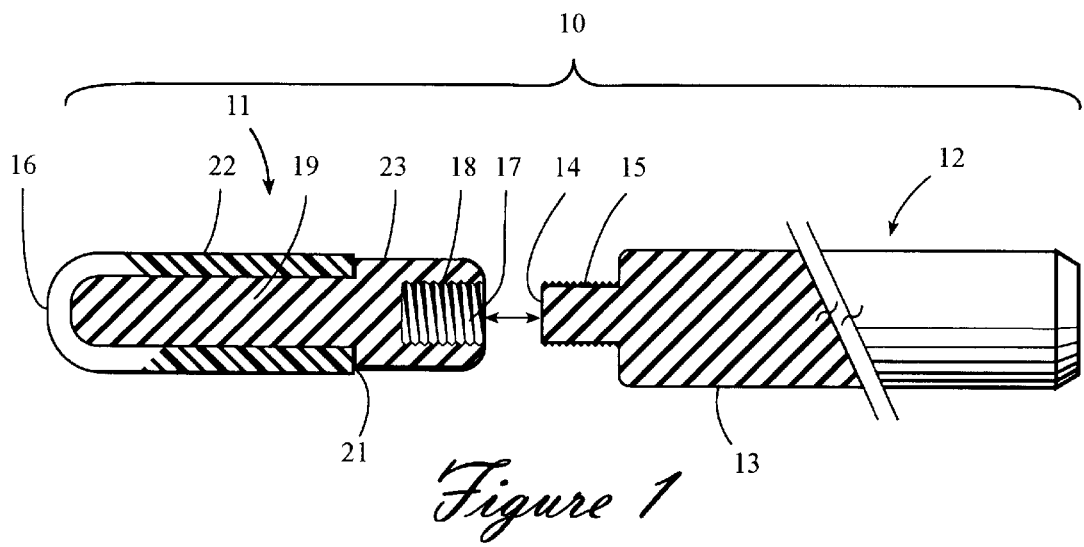
FIG. 1 is a horizontal partially cross-sectional view of a first preferred embodiment of a device in accordance with the present invention.

For the purposes of teaching the principles of the invention, reference will now be made to the embodiment illustrated in the drawings and specific language will be used to describe the same. It will, nevertheless, be understood that no limitation in the scope of the invention is thereby intended, such alterations and modifications in the illustrated device, and such further applications of the principles of the invention as illustrated therein being contemplated as would normally occur to one skilled in the art to which the invention relates.

Referring now to FIG. 1, the device 10 comprises a plug 11 and a plug insertion tool 12. The insertion tool 12 includes a handle portion 13 with a rod 14 extending axially from the distal end thereof which has threads 15 on the outer cylindrical surface thereof. The plug 11 comprises a generally elongate rigid or semi-rigid member having a convex or tapered distal end adapted to facilitate entry into the open end of a tube and a recessed proximal end 17. The recessed proximal end 17 is tapped to provide threads 18 on the inner cylindrical surface thereof which matingly engages the threads 15 on the distal end of the rod 14 protruding from the end of the insertion tool 12.

The plug 11 has an intralumenal portion 11a which extends from step 21 of the plug 11 to the distal end 16. The intralumenal portion 11a is axially symmetric and generally cylindrical but having a non-uniform outer diameter along the length thereof due to the step 21. In operation, when the intralumenal portion 11a of the plug 11 is inserted within the lumen of a tubing having an elastic wall, step 21 aids in ease of plug insertion. The step portion 21 on the intralumenal portion 11a of the plug 11 is a critical feature of the invention. The reduction in outer diameter of the intralumenal portion relative to greater outer diameter of remainder of the intralumenal portion, which spacer portion provides a concentration of energy at the lumen/sheath which interface makes it easier to insert the plug into the tubing than to remove it, the presence of the sheath itself, by virtue of two interfaces theoretically makes removal more difficult.

In the first preferred embodiment of the plug shown in FIG. 1, the intralumenal portion 11a of the plug 11 includes an outer sheath 22 which surrounds the distal end of the intralumenal portion 11a distal to said step portion 21. The outer diameter of the sheath 22 is equal or greater than the outer diameter of the proximal end 23 of the plug 11. Suitable materials or substrates from which the substrate portion 19 of the plug 11 may be fabricated include: (a) long term implantable metal and rigid materials such as titanium or surgical stainless steel; and/or (b) hard plastics and semi-rigid materials such as polyacetal (DELRIN®) or a high durometer silicone. Suitable materials for fabricating the sheath 22 include medical grade elastomers.

Figure 2:
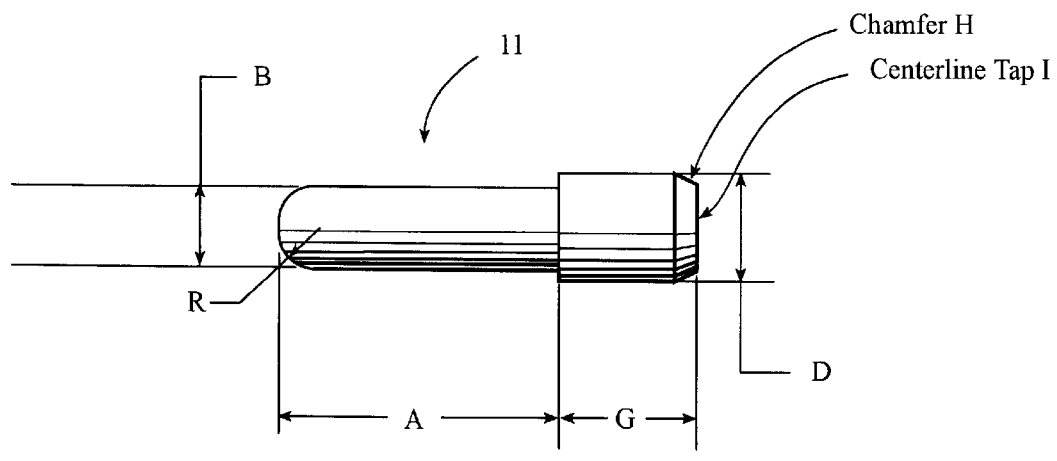
FIG. 2 shows an elevational perspective view of the unitary portion of a plug in accordance with the present invention with the sheath overlying the intralumenal portion removed.

In operation, the device is used to form a leak-proof closure in a tubing having a lumen diameter d. The preferred dimensions of the intralumenal portion of the plug are illustrated in FIG. 2 and are dependent upon the value of d. For the purpose of simplicity, in FIG. 2 the outer sheath 22 (FIG. 1) has been removed from portion 11a of the embodiment of the plug 11 to enable the rendering of the relative dimensions thereof. The outer diameter of the sheath 22 is greater than diameter D of the proximal end 23 of the plug.

The handle portion 13 of the insertion tool 12 is about 1 to 4 inches in length and preferably about 3 inches long having an outer diameter of about 0.4 inches. The dimensions permit the handle portion 13 to be held securely between the fingers and disconnected from the plug after the plug is inserted into the tubing. The plug is preferably made from a biocompatible materials such as titanium substrate 19 and silicone sheath 22.

With reference to FIG. 2, an example of plug dimensions suitable for sealing the open end of an elastic walled tubing having a lumen diameter of 0.05 inches is as follows: A=0.2, B=0.08, D=0.10, G=0.15, chamfer H=0.01 inches×45°, the centerline tap I=0.10 (deep), the radius of curvature R=0.04, the outer diameter of the sheath 22 (not shown in FIG. 2) is greater than 0.10 inches and preferably about 0.12 inches. The sheath 22 (if present) is preferably silicone and extends between the distal end 16 of the plug 11 and terminates proximally at step 21.

Figure 3:
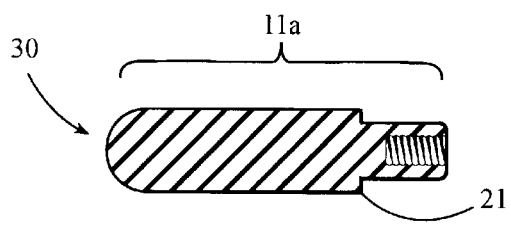
FIG. 3 shows a cross sectional elevational view of a second embodiment of the plug.

In a second embodiment of the plug shown in FIG. 3, the plug 30 is cylindrical and of unitary construction. The dimensions of the second preferred embodiment 30 are identical to the corresponding dimensions of the first embodiment shown in FIGS. 1 and 2. In this second embodiment, however, no sheath is used to cover the intralumenal portion 11a of the plug 30. The outer diameter of the intralumenal portion 11a is greater than the outer diameter of the proximal end 23. The abrupt change in outer diameter of the plug 30 provides a step 21 around the circumference of the plug. The step 21 impedes retraction of the plug 30 from within the lumen of an elastically walled tubing.

A third preferred embodiment of the plug 40 (FIG. 4) utilizes an angled relief on the substrate which is configured similar to an infant "pacifier". This angle, θ (FIG. 5), which is present around the entire 360-degrees of the intralumenal portion of the substrate enhances the force required to pull the plug 40 from the tube. This occurs because the bulbous distal end 41 of the substrate must expand both the proximal portions of the sheath and overlying wall of the elastic tube (not shown) when inserted into the end of the tube and compressed by the (elastic) tubing wall.

Figure 4:
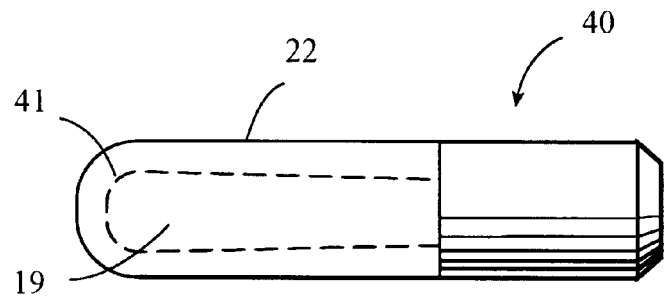
FIG. 4 is a horizontal elevational view of an embodiment of the plug portion of the present invention showing the "pacifier" shape of the intralumenal portion of the plug in phantom.
Figure 5:
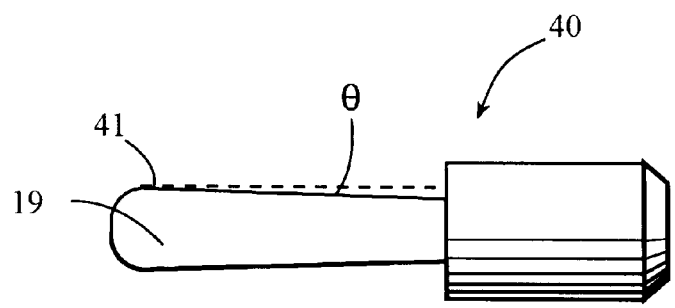
FIG. 5 shows a horizontal elevational view of the plug of FIG. 4 with the sheath removed.
Figure 6:
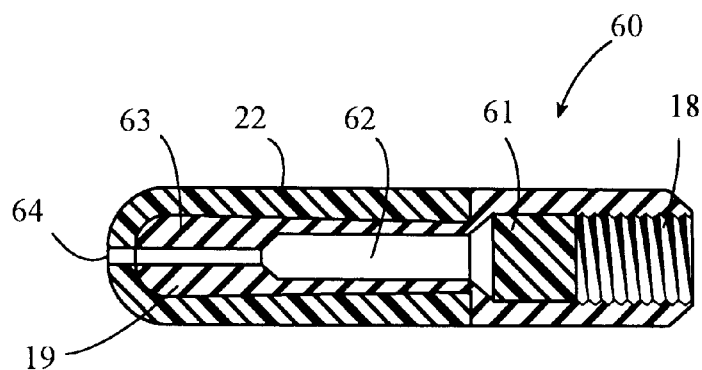
FIG. 6 shows a horizontal cross-sectional view of an embodiment of a self-sealing plug in accordance with the present invention which is adapted to enable injection of a fluid into the lumen of a tubing without requiring the removal of the plug from within the lumen.

A self-sealing plug 60, which is the fourth and most preferred embodiment of the plug, is shown on the accompanying FIG. 6 wherein the self-sealing plug is similar to the "pacifier" configuration of FIGS. 4 and 5 except that the interior of the rigid substrate 19 has been drilled through to provide a cylindrical cavity dimensioned to incorporate a sealing septum 61 therewithin. The septum 61, when press-fit within the cavity drilled into the substrate 19, serves as a barrier for the retention of implant fluid and can be penetrated by a syringe needle when or if fluid needs to be added or removed from the lumen of the tubing or an object in fluid communication with the lumen.

With continued reference to FIG. 6, the centerline tapped threads 18 again may be employed to serve as releasable attachment means adapted to interface to the plug introducer tool, with the distally adjacent cylindrical compartment housing the septum 61. Distal to the septum 61 is a fluid injection port 62 dimensioned to accommodate the tip of a needle (not shown) which, when inserted through the self-sealing septum 61, dispenses a fluid to be introduced into the tubing, such as, for example, to inflate an implant. Immediately distal and adjacent to the injection port 62 is an injection canal 63 which provides fluid communication between the fluid injection port 61 and the lumen of the tube (not shown).

Although the self-sealing plug may incorporate the sheath 22 which is used with the "pacifier" configuration, the sheath 22 is not essential. If a sheath 22 is not used, then the noted angled relief is not required or desired. In this case, the plug exterior would be cylindrical (no step) but still incorporating the convex distal end and chamfer on the proximal end and have a profile similar to the embodiment of the plug shown in FIGS. 1–3. If the sheath is used, an appropriate hole 64 in the most distal end of the sheath is needed for fluid to transfer from the injection canal 63 to the lumen of the tubing.

It should be noted that incorporation of the sheath for any plug design tends to greatly enhance the ease of insertion of the plug into the tubing. The reason for this is that since the sheath and tubing have similar compliance, the tubing does not have to expand as much during insertion compared to an all-metal plug, with the sheath compressing and elongating slightly during insertion and serving as an energy sink.

While particular embodiments of the present invention have been illustrated and described, it would be obvious to those skilled in the art that various other changes and modifications can be made without departing from the spirit and scope of the invention. For example, a bayonet type engagement means may be used to releasably attach the handle portion to the plug. It is therefore intended to cover in the appended claims all such changes and modifications that are within the scope of this invention.

What we claim is:

1. A device forming a leak-proof closure on the end of a tubing having an elastic wall and at least one cylindrical axial lumen, said device comprising, in combination: (a) a plug insertion tool having a handle portion with a plug-engaging portion extending axially therefrom; and (b) a plug comprising a rigid or semi-rigid substrate having a convex distal end and a proximal end and an elongate cylindrical intralumenal portion therebetween, said intralumenal portion having an outer diameter dimensioned to fit snugly within said at least one cylindrical axial lumen of said tubing in leak-proof engagement with said elastic wall of said tubing and wherein said proximal end of said plug is adapted to releasably engage said plug-engaging portion of said insertion tool.

2. The device of claim 1 wherein said plug further includes a cylindrical elastomer sheath overlying said intralumenal portion.

3. The device in accordance with claim 2 wherein said intralumenal portion includes an annular step portion adjacent to said proximal end wherein said annular step portion has an outer diameter which is less than said outer diameter of said intralumenal portion of said plug.

4. The device of claim 1 wherein said plug engaging portion is threaded.

5. The device of claim 1 comprising an axial conduit providing fluid communication between said proximal end and said distal end of said plug and having a self-sealing needle penetrable septum disposed within said conduit.

6. A device forming a leak-proof closure on the end of a tubing having a cylindrical lumen, said device comprising, in combination: (a) a plug insertion tool having a handle portion with a threaded plug-engaging portion extending axially therefrom; and (b) a plug comprising a rigid or semi-rigid substrate having a convex distal end and a proximal end and an elongate cylindrical intralumenal portion therebetween, said intralumenal portion having an outer diameter dimensioned to fit snugly within said cylindrical lumen of said tubing in leak-proof engagement with said wall of said tubing and wherein said proximal end of said plug is adapted to releasably engage said threaded plug-engaging portion of said insertion tool.

7. The device of claim 5 further comprising an axial conduit providing fluid communication between said proximal end and said distal end of said plug and having a self-sealing needle penetrable septum disposed within said conduit.

8. A device forming a leak-proof closure on the end of a tubing having a cylindrical lumen, said device comprising, in combination: (a) a plug insertion tool having a handle portion with a threaded plug-engaging portion extending axially therefrom; and (b) a plug comprising a rigid or semi-rigid substrate having a convex distal end and a proximal end and an elongate axially symmetric bulbous intralumenal portion therebetween, said intralumenal portion having an outer diameter dimensioned to fit snugly within said cylindrical lumen of said tubing in leak-proof engagement with said wall of said tubing and wherein said proximal end of said plug is adapted to releasably engage said threaded plug-engaging portion of said insertion tool.

9. The device of claim 8 further comprising an axial conduit providing fluid communication between said proximal end and said distal end of said plug and having a self-sealing needle penetrable septum disposed within said conduit.

10. A plug forming a leakproof closure on the end of a tubing having an elastic wall and a cylindrical lumen, said plug comprising an elongate axially symmetric elastomeric member having a proximal end and a convex distal end and a bulbous intralumenal portion therebetween, said intralumenal portion having an outer diameter dimensioned to fit snugly within said cylindrical lumen of said tubing in leak-proof engagement with said wall of said tubing and wherein said proximal end of said plug is adapted to releasably engage a plug insertion tool.

11. The plug of claim 10 further comprising an axial conduit providing fluid communication between said proximal end and said distal end of said plug and having a self-sealing needle penetrable septum disposed within said conduit.

* * * * *